(12) United States Patent
Endo

(10) Patent No.: US 7,075,090 B2
(45) Date of Patent: Jul. 11, 2006

(54) RADIOLOGICAL IMAGING APPARATUS AND RADIOLOGICAL IMAGING METHOD

(75) Inventor: Tadao Endo, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 197 days.

(21) Appl. No.: 10/464,012

(22) Filed: Jun. 18, 2003

(65) Prior Publication Data

US 2004/0008813 A1    Jan. 15, 2004

(30) Foreign Application Priority Data

Jun. 19, 2002    (JP) ............................. 2002-178800

(51) Int. Cl.
*H04N 5/00* (2006.01)
(52) U.S. Cl. .............................. 250/370.11; 250/370.07
(58) Field of Classification Search ........... 250/370.11, 250/370.07, 370.09, 580; 378/57, 98.8, 19
See application file for complete search history.

(56) References Cited

U.S. PATENT DOCUMENTS

| | | | |
|---|---|---|---|
| 6,163,029 A | 12/2000 | Yamada et al. ........ | 250/370.09 |
| 6,185,274 B1 * | 2/2001 | Kinno et al. ................ | 378/98.8 |
| 2004/0017891 A1 * | 1/2004 | Endo .......................... | 378/98.8 |
| 2004/0051063 A1 * | 3/2004 | Shoji ........................... | 250/580 |

* cited by examiner

*Primary Examiner*—Otilia Gabor
(74) *Attorney, Agent, or Firm*—Morgan & Finnegan, L.L.P.

(57) ABSTRACT

A radiological imaging apparatus and method allows an operator to select between moving-picture imaging and still-picture imaging modes using the same apparatus so to provide radiological imaging having a picture quality equal to that of conventional radiological film imaging techniques but with a smaller, lighter and more compact equipment configuration. The apparatus employs photoelectric converters arranged in a two-dimensional matrix array for converting radiation into electrical signals, a read-out circuit for reading the signal output from the photoelectric converters, variable gain amplifiers upstream of an analog multiplexer and a buffer amplifier downstream of the multiplexer for outputting serially converted signals. The method involves setting the moving-picture mode gain Gf so as to be greater than the still-picture mode gain Gs, in order to obtain sharper images without exposing the subject to unnecessarily high levels of radiation.

10 Claims, 6 Drawing Sheets

FIG. 4

| FRAME NO.: start | 1 | 2 | 3 | ... | 48 | 49 | 50 | 51 | end |
|---|---|---|---|---|---|---|---|---|---|
| MODE: start | MOVING PICTURE | MOVING PICTURE | MOVING PICTURE | ... | MOVING PICTURE | MOVING PICTURE | MOVING PICTURE | STILL PICTURE | end |
| SENSOR: start | XR | XR | XR | ... | XR | XR | XR | XR | end |
| GAIN: start | Gf | Gf | Gf | ... | Gf | Gf | Gf | Gs | end |

RADIOLOGICAL IMAGING APPARATUS AND RADIOLOGICAL IMAGING METHOD

FIELD OF THE INVENTION

The present invention relates to a radiological imaging apparatus and method, and more particularly, to a radiological imaging apparatus and method used in medical X-ray equipment, industrial non-destructive testing devices and the like.

BACKGROUND OF THE INVENTION

With the conventional still-picture X-ray technology currently in use, the so-called film-based technique is the most prevalent. In this technique, the patient is exposed to X-rays and the X-rays that pass through the body are then exposed onto a sheet of film. The film has the function of displaying and recording information, and is widely used throughout the world due to its capacity to be enlarged, its high degree of gradation, its light weight and ease of handling. On the other hand, the technique suffers from several disadvantages, including a complicated process of developing the image, the problem of long-term storage, and the time and effort involved in manual search and retrieval of the physical images.

By contrast, moving image photographic systems rely mainly on image intensifier (I.I). Since I.I uses the photoelectron multiplier effect inside the device, it generally has good sensitivity and has the additional advantage of exposing the patient to lower levels of radiation. The I.I not only provides the physician with a see-through image of the patient but also, due to the conversion of the CCD analog output to digital output (a process referred to here as digitization), makes possible the computerized recording, display and storage of such data.

However, because medical diagnosis requires a high degree of gradation, even with I.I, film is often used for still picture imaging. In addition, such systems suffer from the following disadvantages: peripheral image distortion due to the characteristics of the optical system, low contrast and large equipment size.

Recently, with a growing need to digitize X-ray images inside the hospital itself, in place of film, X-ray imaging devices that use an X-ray sensor with solid-state image sensing elements arrayed two-dimensionally to convert the X-ray image into electrical signals have begun to be used. Since the X-ray image can then be replaced with digital information, image information can be sent instantaneously to distant locations, with the advantage of being able to provide state-of-the-art, high-quality diagnostics even to remote areas. Moreover, if no film is used the space previously required for its storage can be turned to other, more productive uses. If in the future it becomes possible to introduce more advanced and sophisticated image processing techniques, it is possible that diagnostics may to some extent be computerized and therefore automated, without the intervention of a radiologist.

Moreover, in recent years, with the use of amorphous thin-film semiconductors in solid-state image sensing elements, X-ray imaging devices capable of taking still pictures have been developed. Using amorphous silicon thin-film semiconductor production technology, photos exceeding 40 cm a side and capable of completely imaging the human torso have been commercialized. Since the production process itself is relatively simple, it is expected that inexpensive detectors based on this technique will become available in the not-so-distant future. In addition, since amorphous silicon can be produced in thin glass sheets having a thickness of 1 mm or less, the detector itself can be made very thin and compact, for greater ease of handling.

More specifically, FIG. 5 shows the internal structure of a read-out circuit of an X-ray imaging device using an amorphous silicon thin film semiconductor for the solid-state image sensing elements. In FIG. 5, RES1–RES3 are reset switches that reset the signal lines M1–M3, A1–A3 are amplifiers that amplify the signals of M1–M3, CL1–CL3 are sample-hold capacitors that temporarily store the signals amplified by amplifiers A1–A3, Sn1–Sn3 are sample-hold switches, B1–B3 are buffer amplifiers, Sr1–Sr3 are switches for the serial conversion of parallel signals, reference numeral 103 denotes a shift resister for applying pulses to the switches Sr1–Sr3 for serial conversion, and reference numeral 104 denotes a buffer amplifier for outputting the serially converted signals.

FIG. 6 is a timing chart showing the operation of an X-ray imaging apparatus having the read-out circuit shown in FIG. 5. First, as for the photoelectric conversion interval (given in the diagram as the X-ray exposure interval): In a state in which the TFT are all OFF and when the light source (X-rays) are turned ON in pulses, each of the respective photoelectric converters is struck by the light and a signal electric charge comparable to the amount of light is stored in each of the respective converter capacitors. If a fluorescent material is used to convert the X-rays into visible light, then either a light-guiding member for guiding the light made visible in proportion to the number of X-rays to the photoelectric converters may be used or the fluorescent material may be disposed near the electrodes of the photoelectric converters.

It should be noted that the signal electrical charge is held in the converter capacitor after the light source is OFF.

Next, as for the read-out interval: The read-out is accomplished at the S1-1–S3-3, one row at a time, starting with row S1-1–S1-3, then with row S2-1–S2-3, and finally with row S3-1–S3-3. First, a gate pulse is applied from SR1 to the T1-1–T1-3 (TFT) switch gate lines in order to read out the first row S1-1–S1-3. Doing so turns T1-1–T1-3 ON and the signal electrical charges that had been stored in S1-1–S1-3 is sent to the signal lines M1–M3 to which read-out capacitors CM1–CM3 (see FIG. 1) have been added, so that the signal electrical charges are sent to the read-out capacitors CM1–CM3 via the TFT. For example, read-out capacitor CM1 added to signal line M1 is the (three-) sum total of the T1-1–T1-3 gate-source interelectrode capacitance (Cgs). Amplifiers A1–A3 amplify the signal electrical charge sent to signal lines M1–M3.

The amplified signal electrical charge sent to capacitors CL1–CL3 both turns OFF and holds SMPL signal OFF. Next, by imparting a pulse from a shift resister 103 to switches Sr1, Sr2 and Sr3 (in that order) the signals held at CL1–CL3 are then output from an amplifier 104 in the order CL1, CL2 and CL3. Since analog signal outputs B1, B2 and B3 are output from the amplifier 104, the entire unit, including the shift resister 103 and the switches Sr1–Sr3, is called an analog multiplexer. Ultimately, one row's worth of photoelectric conversion signals (S1-1, S1-2, S1-3) is output in sequence by the analog multiplexer. The read-out of the second row S2-1–S2-3 and the read-out of the third row S3-1–S3-3 are carried out in the same way as the read-out of the first row described above.

If the signals at signal lines M1–M3 are sampled and held at CL1–CL3 by the first row's SMPL signal, then the signal lines M1–M3 can be reset to ground electric potential by a CRES signal and thereafter a G2 gate pulse can be applied. In other words, second-row signal electrical charges from the photoelectric converters S2-1–S2-3 can be transmitted by the SRI while at the same time the first row's signals are being serially converted by the SR2. In so doing, all the signal electrical charges of the first through third rows of photoelectric converters can be output.

Although moving image photography employing I.I has a higher sensitivity than X-ray imaging apparatuses employing amorphous silicon, as described above, I.I-based imaging suffers from the disadvantages of peripheral image distortion, low contrast and, when using photographic film, large and unwieldy equipment size.

By contrast, X-ray imaging apparatuses introducing amorphous silicon thin film semiconductors have been commercialized and provide still images of a picture quality equal or superior to that of the conventional film-based imaging method. However, there has been no commercialization of see-through moving pictures. One reason for this is that moving picture imaging exposes the patient to greater levels of radiation. Reducing the levels of radiation exposure only worsens the signal-to-noise ratio (S/N). Also, the scan speed (that is, the frame rate) of such moving picture imaging must usually be much greater (that is, much faster) than is the case with sill picture imaging, which means that the imaging apparatus's frequency band must be broadened. However, broadening the imaging apparatus's frequency band increases the so-called white noise such as shot noise and Johnson noise, thus degrading the S/N.

In FIG. 5, there are three input lines and one output line, with the parallel signals being converted to serial signals by an analog multiplexer 103 (Sr1–Sr3). Normally, amplifiers A1 and B1 are set to frequency bands at which they can amplify signals from a photoelectric converter circuit within a single line operating time interval. Broadening the band beyond what is necessary only increases the Johnson noise (that is, the thermal noise, which is electrical noise produced by thermal agitation of electrons in conductors and semiconductors), which is undesirable. On the other hand, the analog signals must be serially converted by amplifiers and multiplexer (103, Sr1–Sr3) at a later stage than that of the analog multiplexer, so the frequency band must be set broader than the frequency bands of the A1 and A3 amplifiers.

Generally, the Johnson noise (Vrms) is expressed by the following equation:

$$Vrms = (4KTRB)^{1/2}$$

where K is the Boltzmann constant, T is absolute temperature, R is resistance and B is the frequency band. Portion $(4KTR)^{1/2}$ unmultiplied by $B^{1/2}$ is called the noise density.

An operational amplifier generates Johnson noise from all the components that compose it, such as the ON-resistance of the transistor that forms the first stage of the amplifier and the input resistance and feedback resistance not shown in the FIG. 5, such noise being proportional to the square root of the individual frequency bands.

For example, in FIG. 5, amplifier 104 serially converts three pixels, so it requires a frequency band that is at least three times greater than that of amplifier A1. This means that, as a result, when the A1 amplifier noise density and the 104 amplifier noise density are equal, the 104 amplifier noise (that is, the effective value) increases.

The chest X-rays used in hospitals, because they are so often used for chest X-rays, are said to require a photosensitive area of at least 40 cm×40 cm. In that case, the pixel pitch should be no greater than 200 μm, preferably less if possible. For example, an area measuring 40 cm×40 cm with a pitch of 200 μm would require 2,000×2,000 pixels=4,000,000 pixels. In other words, the number of line inputs in the read-out circuit in FIG. 5 would be 2,000 (pixels).

Accordingly, it is not practical to produce an arrangement calling for 2,000 input lines over 40 cm on a single read-out circuit, so ordinarily a design is used in which the load is apportioned among a plurality of read-out circuits. For example, if divided among ten read-out circuits, the number of inputs is 200 per 1 output, which is a more realistic range. In this case, the 104 amplifier requires a frequency band that is 200 times that of the A1 amplifier. Assuming the 104 amplifier and the A1 amplifier have the same noise density, the noise effective value will work out to be $200^{1/2} \approx 14$ times for the 104 amplifier.

SUMMARY OF THE INVENTION

The present invention has been conceived in light of the foregoing considerations.

According to one aspect of the present invention, preferably, a radiological imaging apparatus for forming X-ray images comprises:

a radiation detection unit composed of a plurality of photoelectric converters arrayed in a matrix-like formation for the purpose of detecting and converting radiation from an irradiated subject into electrical signals;

a drive control unit operatively connected to the radiation detection unit for the purpose of controlling movement of the radiation detection unit; and a read-out unit operatively connected to the radiation detection unit for reading the electrical signals output by the radiation detection unit, the apparatus selecting between a moving-picture mode and a still-picture mode, the read-out unit comprising:
a variable amplifier unit with variable gain; and
a control unit for controlling the gain on the variable amplifier unit, the control unit's variable amplifier unit's gain control setting a gain Gf for the moving-picture mode to be greater than a gain Gs for the still-picture mode.

According to another aspect of the present invention, preferably, a radiological imaging method comprises the steps of:

selecting between a still-picture mode and a moving-picture mode using a radiological imaging apparatus equipped with a plurality of radiation detection units for converting radiation into one or more electrical signals; and employing a variable gain control so that a gain Gf during the moving-picture mode is set to be greater than a gain Gs during the still-picture mode.

Other features, effects and advantages of the present invention will be apparent from the following description, taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention, in which:

FIG. 4 is a timing chart of the operation of an X-ray imaging apparatus according to one embodiment of the present invention;

DETAILED DESCRIPTION OF THE PREFERRED EMBODIMENTS

Figure 1:
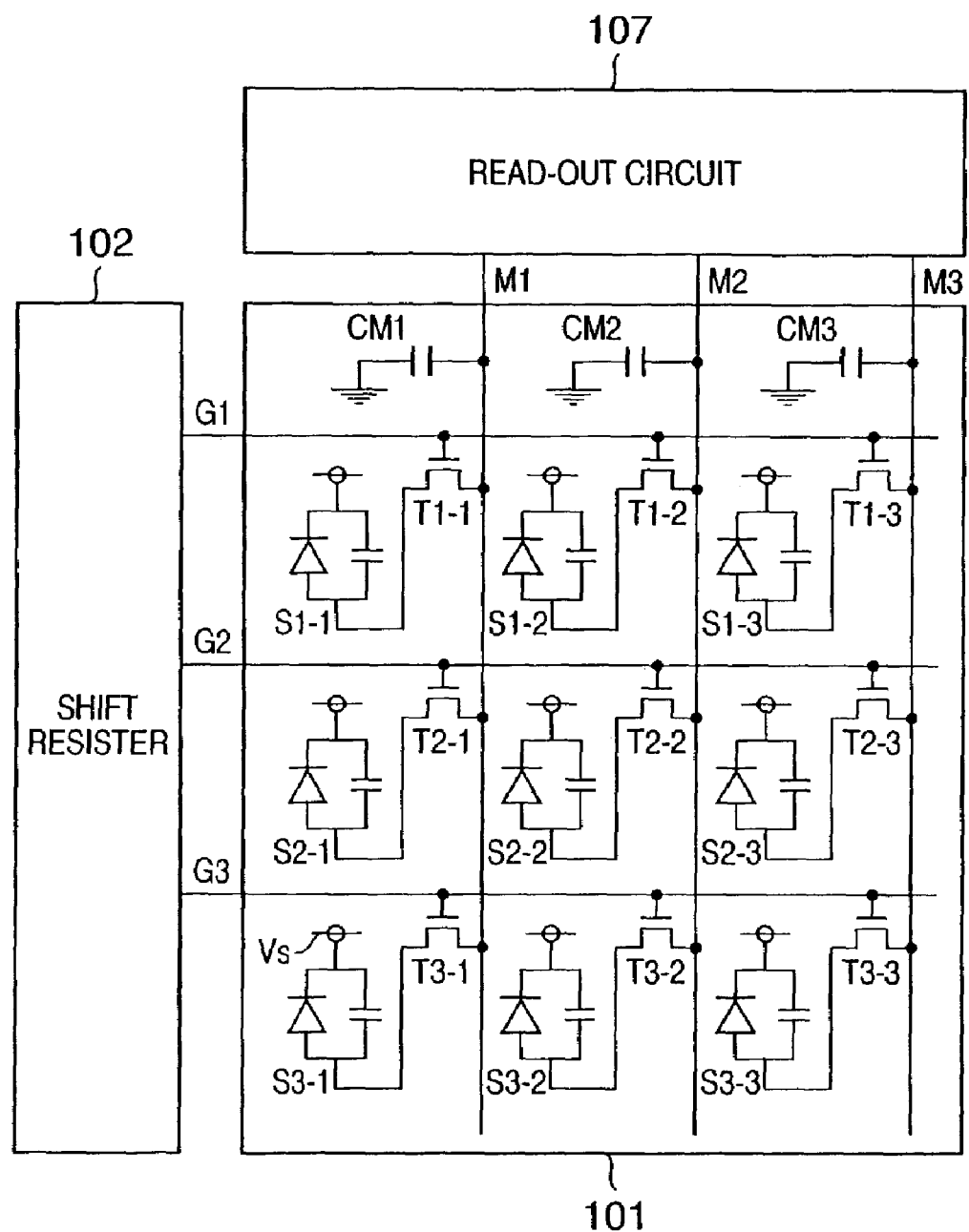
FIG. 1 is a circuit diagram of an X-ray imaging apparatus employing an amorphous silicon thin film semiconductor according to one embodiment of the present invention.

Preferred embodiments of the present invention are described in detail in accordance with the accompanying drawings, with reference in the first instance to FIG. 1.

FIG. 1 is a circuit diagram of an X-ray imaging apparatus employing an amorphous silicon thin film semiconductor according to one embodiment of the present invention, in which the apparatus uses photoelectric converters to take visible light and convert that light into electrical signals.

In this X-ray imaging device, an operator can select between a moving-picture mode and a still-picture mode. It should be noted that FIG. 1 does not show the fluorescent material used to convert the X-rays into visible light, and although the present embodiment is described with reference to X-ray imaging, the present invention is not limited to such but should be understood as being equally applicable to instances involving other types of radiation, such as, for example, alpha-rays, beta-rays or gamma-rays.

In FIG. 1, reference symbols S1-1–S1-3 denote photoelectric converters arranged in a two-dimensional array, T1-1–T1-3 denote switches (that is, thin-film transistors, or TFT), G1–G3 denote gate lines that turn the TFT ON/OFF and M1–M3 denote signal lines. Each one of the photoelectric converters is denoted by a photodiode and a capacitor connected in parallel, and is given a reverse bias. That is, the cathode terminal of the photodiode is given a positive (+) bias. The bias lines typically involve joint (common) lines, which for convenience only are not shown in FIG. 1. The photoelectrically converted electrical charges are stored in the capacitors. The entire assemblage of S1-1–S1-3, T1-1–T1-3, G1–G3, signal lines M1–M3 and Vs lines is together called a radiation detection circuit or a photoelectric converter circuit. Reference numeral 102 denotes a shift resister that applies pulses to the gate lines G1–G3 and controls the driving of the photoelectric converters S1-1–S1-3. Reference numeral 107 denotes a read-out circuit that amplifies and serially outputs the parallel signal output of the signal lines M1–M3 inside the photoelectric converter circuit 101.

Each of the photoelectric converters has a wavelength converter for converting the radiation to visible light and a photoelectric converter portion that converts the visible light received into electrical signals. The matrix material of the wavelength converter is a material selected from the group consisting of $Gd_2O_3$, $Gd_2O_2S$ and CsI. The photoelectric converter portion is composed mainly of amorphous silicon. Each of the photoelectric converters is made of a material selected from the group consisting of amorphous silicon, gallium arsenic, mercury iodide and lead iodide. It should be noted that although for convenience of explanation the foregoing description uses the example of a 3×3-pixel photoelectric converter, in reality many more photoelectric converters are arrayed.

Figure 2:
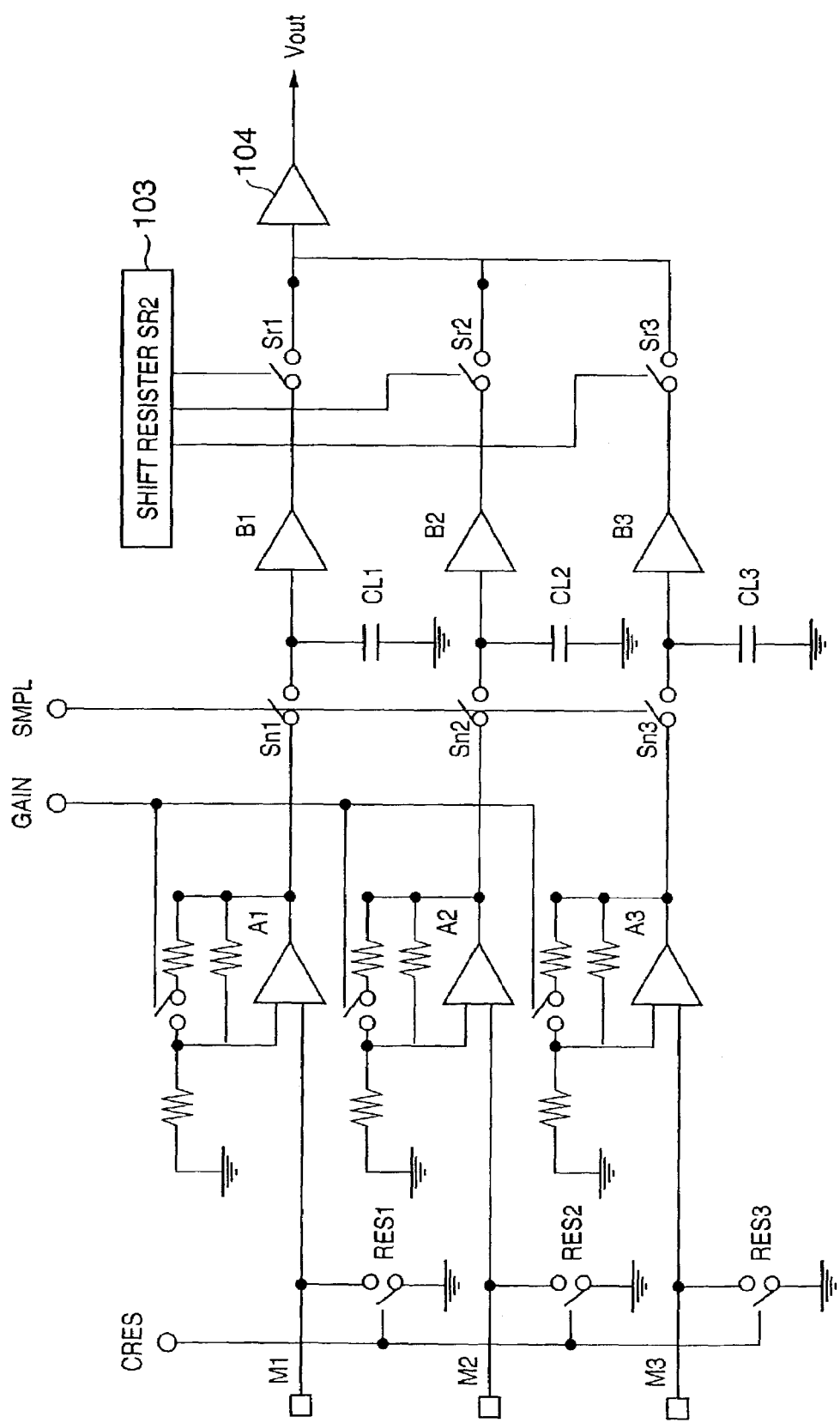
FIG. 2 is a circuit diagram showing the internal structure of the read-out circuit of FIG. 1.

FIG. 2 is a circuit diagram showing the internal structure of the read-out circuit of FIG. 1. In FIG. 2, RES1–RES3 are reset switches that reset the signal lines M1–M3, A1–A3 are amplifiers that amplify the signals of M1–M3, CL1–CL3 are sample-hold capacitors that temporarily store the signals amplified by amplifiers A1–A3, Sn1–Sn3 are sample-hold switches, B1–B3 are buffer amplifiers, Sr1–Sr3 are switches for the serial conversion of parallel signals, reference numeral 103 denotes a shift resister for applying pulses to the switches Sr1–Sr3 for serial conversion, and reference numeral 104 denotes a buffer amp for outputting the serially converted signals. An analog multiplexer is formed from the switches Sr1–Sr3 and the shift resister 103.

Figure 3:
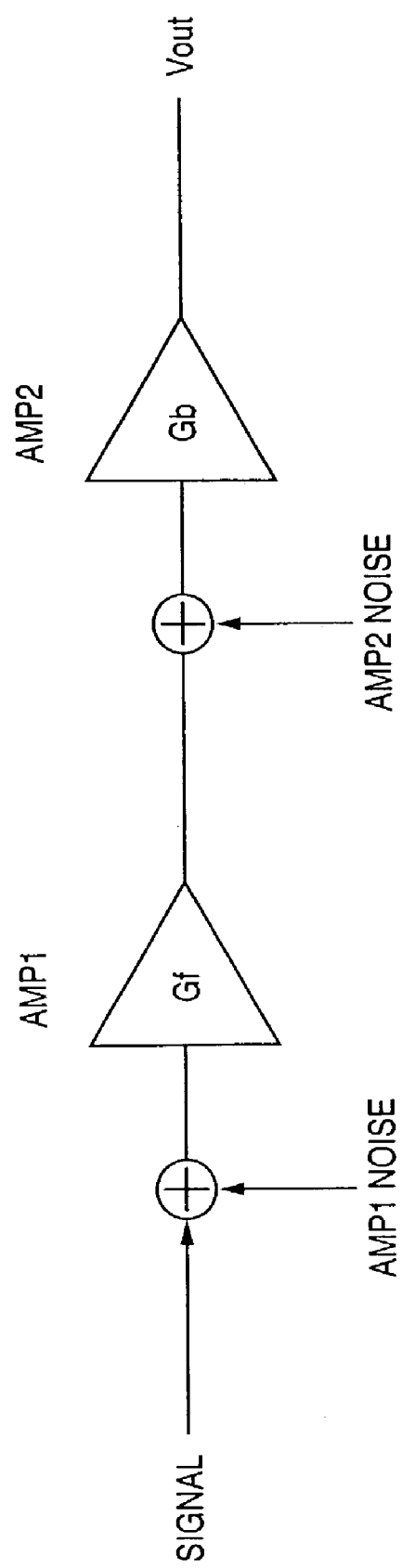
FIG. 3 is a simplified circuit diagram of the read-out circuit of the X-ray imaging apparatus according to one embodiment of the present invention, in which the multiplexer has been eliminated.
Figure 5:
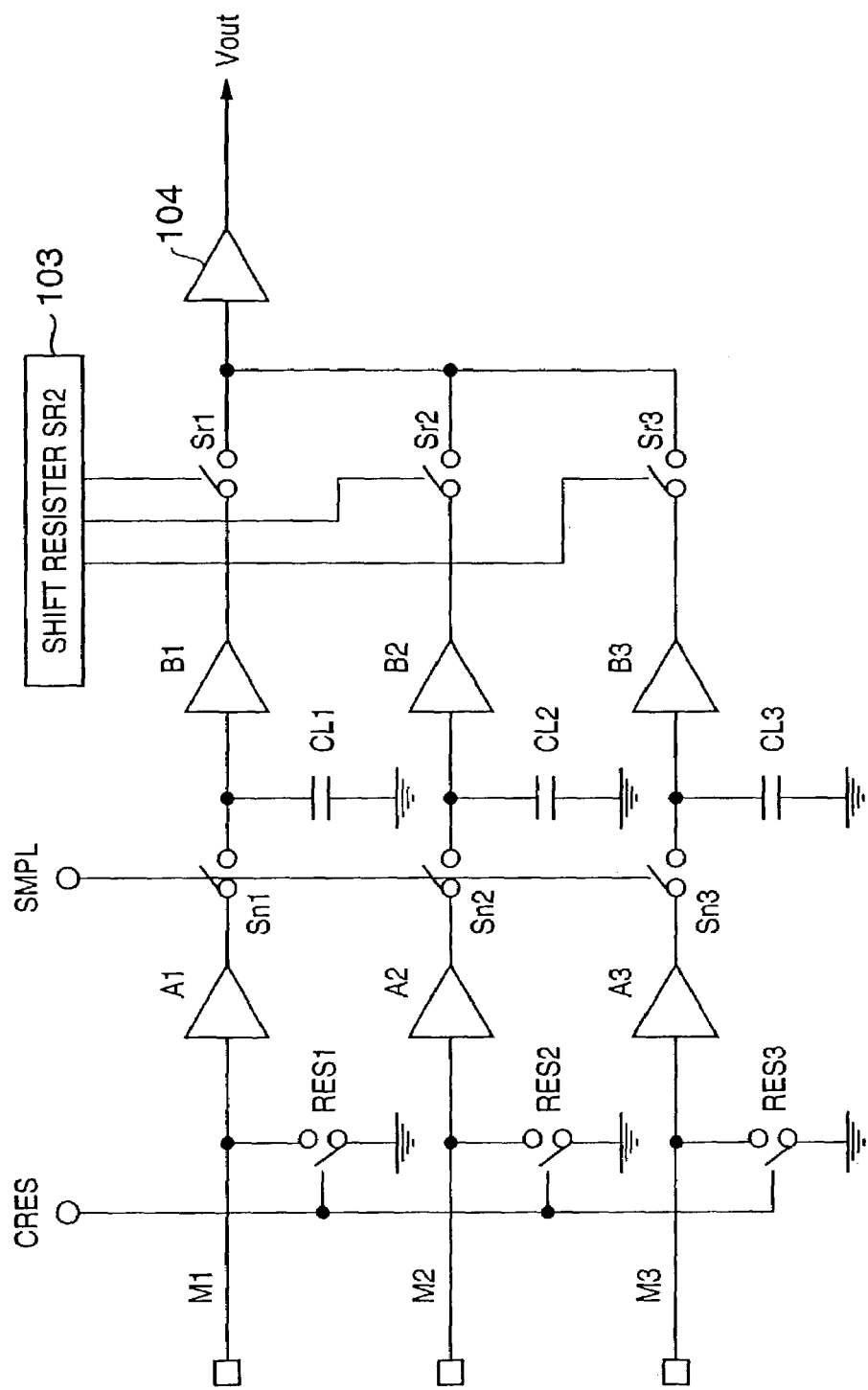
FIG. 5 is a diagram showing the internal structure of a read-out circuit of an X-ray imaging device using an amorphous silicon thin film semiconductor for the solid-state image sensing elements.

FIG. 3 is a simplified circuit diagram of the read-out circuit of the X-ray imaging apparatus according to one embodiment of the present invention, in which the multiplexer has been eliminated to simplify the description. If the input conversion noise density of AMP1 upstream of the analog multiplexer is Nf ($V/Hz^{1/2}$), the frequency band is Bf (Hz) and the gain is Gf (multiple), and if the input conversion noise density of AMP2 downstream of the analog multiplexer is Nb ($V/Hz^{1/2}$), the frequency band is Bb (Hz) and the gain is Gb (multiples), then the volume of noise Vf (Vrms) at the upstream amplifier and the volume of noise Vb (Vrms) at the downstream amplifier may each be expressed by the following equations:

$$Vf = Gf \cdot (Nf^2 \cdot Bf)^{1/2} = Gf \cdot N1 \, (Vrms)$$

$$Vb = Gb \cdot (Nb^2 \cdot Bb)^{1/2} = Gb \cdot N2 \, (Vrms)$$

where $N1 = (Nf^2 \cdot Bf)^{1/2}$ and $N2 = (Nb^2 \cdot Bb)^{1/2}$.

By contrast, at AMP2, the noise is double (Gb) the noise at AMP1, so the total of the two noise volumes $V_{out(noise)}$ at the output is $$V_{out\,(noise)} = [(Gb \cdot Vf)^2 + Vb^2]^{\frac{1}{2}}$$

$$= [(Gb \cdot Gf \cdot N1)^2 + (Gb \cdot N2)^2]^{\frac{1}{2}}$$

At the same time, the signal volume $V_{out(signal)}$ is doubled by Gf and Gb at AMP1 and AMP2, respectively, so the $V_{out(signal)} = Gf \cdot Gb \cdot V_{in(noise)}$. Therefore, the S/N is expressed by the following equation:

$$\frac{S}{N} = \frac{V_{out\,(signal)}}{V_{out\,(noise)}}$$

$$= \frac{V_{in\,(signal)}}{\left[N1^2 + \left(\frac{N2}{Gf}\right)^2\right]^{\frac{1}{2}}}$$

In short, the larger the gain Gf set at AMP1, the better the S/N.

In the present embodiment, the amplifiers A1–A3 provided upstream of the analog multiplexer are composed of non-inverted amplifiers, and the feedback resistance is connected in parallel by the control signal GAIN. In other words, the rate of amplification (gain) can be varied by the control signal GAIN. As an example, if the three resistances connected to A1 all have the same value, the gain can be doubled or tripled. By selecting suitable resistance values the switching gain type can be set largely at will.

Figure 6:
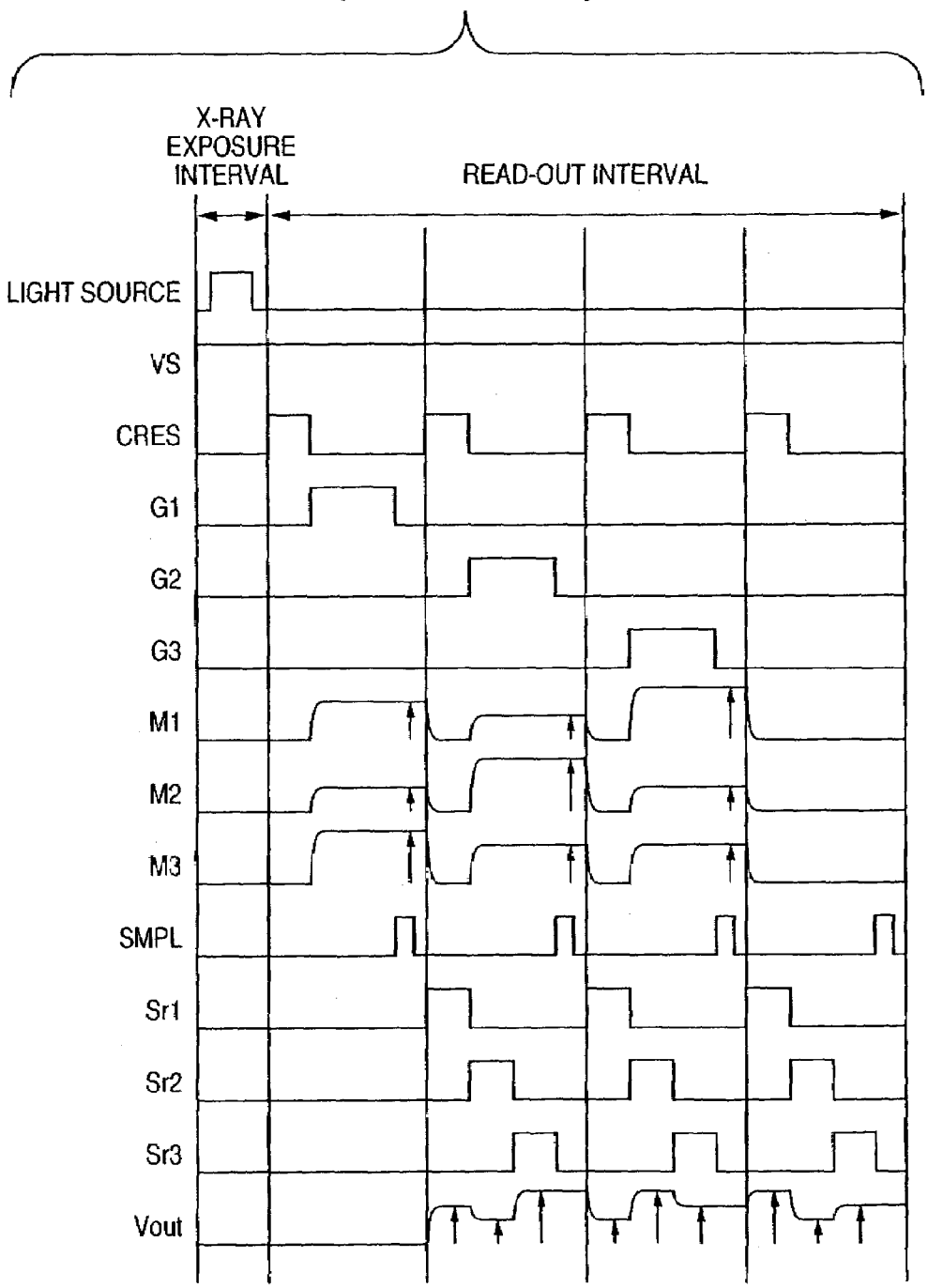
FIG. 6 is a timing chart showing the operation of an X-ray imaging apparatus having the read-out circuit shown in FIG. 5.

FIG. 4 is a timing chart of the operation of an X-ray imaging apparatus according to one embodiment of the present invention. Here, the moving-picture mode is carried out 50 frames at a time, after which the still-picture mode is executed at the 51st frame. Time, in this diagram, proceeds from left to right across the page, and the X-ray exposure interval and read-out interval of the conventional example of FIG. 6 are here designated by the reference symbols "X" and "R", respectively.

In the moving-picture mode, the X-ray exposure operation "X" and the read-out operation "R" are alternated and repeated. The distinctive feature of the present embodiment is that the gain of the amplifiers A1–A3 shown in FIG. 1 are connected to Gf, and Gf is set greater than the Gs set by the still-picture mode performed at the 51st frame. In so doing, for an identical given signal (S), the moving-picture mode S/N is greater than the still-picture mode S/N, thus improving picture quality.

It should be noted that the same description as that provided above also holds true for the still-picture mode as well, that is, the greater the gain set for amplifiers A1–A3, the better the S/N and hence the better the picture quality. Unlike in the moving-picture mode, however, in the still-picture mode only a single frame of X-rays are shot, so in order to obtain a sharper image a larger number of X-rays than for a single moving-picture frame must be used. Ordinarily, read-out circuit amplifiers such as A1–A3 and B1–B3 are set to a non-saturation level of gain.

By contrast, in the moving-picture mode X-rays are being shot continuously, so in order to reduce the level of X-rays to which the patient is exposed by even a small amount it is necessary to reduce the number of X-rays per each frame. In other words, the number of X-rays used per frame in the moving-picture mode is less than the number of X-rays used in the still-picture mode. For example, if the number of X-rays used in the moving-picture mode is ⅓ the number of X-rays used in the still-picture mode, then the gain Gf in the moving-picture mode can be set to be 30 times greater than the gain Gs in the still-picture mode.

In FIG. 4, a description is given of the timing of the operation of shifting from the moving-picture mode to the still-picture mode. A situation is assumed in which the physician or radiologist monitors a see-through image of the subject in the moving-picture mode in order to determine exactly where and when the shift to the still-picture imaging mode should be undertaken, at which point and time a shift-to-still-picture mode trigger, or command, issued from the physician or radiologist is sent to the X-ray imaging apparatus. Alternatively, the see-through moving image may not only be observed and monitored but may also be recorded and stored on a suitable storage medium, as the user prefers and circumstances permit or require. It should also be noted that the apparatus not only enables a shift from the moving-picture mode to the still-picture mode but also allows dedicated use in either the moving-picture mode or in the still-picture mode, again as the user prefers and circumstances permit or require.

It should be noted that the operation depicted in FIG. 4 is described above with reference to a situation in which, in the read-out operation of the moving-picture mode, the X-ray exposure operation "X" and the photoelectric converter circuit read-out operation "R" are alternated repeatedly. However, as can be appreciated by those of ordinary skill in the art, if the read-out operation interval "R" is kept constant, then it is not necessary to shoot the X-rays in pulses as shown in FIG. 4. Instead, the X-ray generator may be fired continuously so as to produce a steady stream of X-rays. In such a case, the moving-picture mode read-out cycle can be shortened and the moving image frame rate can be increased.

Also, in FIG. 4, no distinction is made between the moving-picture mode read-out operation "R" and the still-picture mode read-out operation "R", and both types of read-out operations have been designated by the same reference symbol "R". However, it is not necessary for the time interval needed for these read-out operations to be the same. The read-out operation interval required for moving-picture imaging, though it varies according to which part of the patient's body is to be imaged, generally lasts from 10 msec to 200 msec. By contrast, the read-out operation time interval required for still-picture imaging is generally longer than that for moving-picture imaging, and is set at from 100 msec to 1,000 msec, depending on the switch characteristics, the read-out circuit amplifier characteristics and so forth.

In FIG. 1, the control signal GAIN switches the A1–A3 gain between two types. However, as can be appreciated by those of ordinary skill in the art, the present invention is not limited to such a configuration. Instead, depending on the volume of X-rays in the moving-picture mode, a plurality of gain switch types may be prepared. In such cases, a resistance and a switch are added to the feedback terminals of amplifiers A1–A3 of FIG. 2 and not one but a plurality of gain terminals are used.

Also, in FIG. 2, only amplifiers A1–A3 have been given the ability to switch the gain. However, it is also possible to provide amplifiers B1–B3 with a switching function as well. In other words, in the present embodiment, the point of connection of the amplifiers having the ability to switch gain may just as easily be made upstream of the analog multiplexer as downstream of the analog multiplexer.

As described above, according to the X-ray imaging apparatus and method of the present invention, by providing amplifiers A1–A3 upstream of the analog multiplexer with the ability to switch the gain, the S/N in the moving-picture mode can be improved by setting the gain higher in the moving-picture mode than in the still-picture mode. Moreover, both moving images and still images can be acquired with one and the same apparatus, thus making it possible to obtain picture quality equivalent to that of conventional film but with an apparatus arrangement that is lighter and more compact than the conventional I.I imaging equipment.

The present invention thus provides a radiological imaging apparatus and method of the present invention in which, when creating a see-through image of a subject, an operator can select between a moving-picture mode and a still-picture mode using one and the same imaging apparatus and still acquire still-image picture quality equivalent to that of film-based X-ray photography, yet with smaller and more lightweight and compact equipment than is the case with conventional I.I imaging equipment and techniques.

As many apparently widely different embodiments of the present invention can be made without departing from the spirit and scope thereof, it is to be understood that the invention is not limited to the specific preferred embodiments described above thereof except as defined in the claims.

What is claimed is:

1. A radiological imaging apparatus for forming X-ray images, comprising:
   a radiation detection unit composed of a plurality of photoelectric converters arrayed in a matrix-like formation, configured to detect and convert radiation from an irradiated subject into electrical signals;
   a drive control unit operatively connected to said radiation detection unit, configured to control movement of said radiation detection unit; and
   a read-out unit operatively connected to said radiation detection unit, configured to read the electrical signals output by said radiation detection unit,
   said read-out unit comprising:
   a first amplifier unit with variable gain;
   a control unit, configured to control the gain of said first amplifier unit;
   a sample-hold unit disposed downstream of said first amplifier unit, configured to hold a signal amplified by said first amplifier;
   a multiplexer disposed downstream of said sample-hold unit, configured to convert parallel signals output from said sample-hold unit into a serial signal; and
   a second amplifier unit disposed downstream of said multiplexer;
   wherein a frequency band of said first amplifier unit is narrower than that of said second amplifier unit, and
   a gain Gf of said first amplifier unit for a moving-picture mode is set to be greater than a gain Gs of said first amplifier unit for a still-picture mode by said control unit.

2. The radiological imaging apparatus of claim 1, wherein said second amplifier unit has a fixed gain.

3. The radiological imaging apparatus of claim 1, wherein when imaging a still picture, a moving image is acquired during the gain (Gf) is set to said first amplifier unit in the moving-picture mode and the apparatus then switches to the still-picture mode to set the gain (Gs) to said first amplifier unit so as to obtain a still image in response to a still picture imaging request.

4. The radiological imaging apparatus of claim 1, wherein the radiation detection unit further comprises a wavelength converter for converting said radiation into visible light and a photoelectric converter for detecting and convening said visible light into one or more electrical signals.

5. The radiological imaging apparatus of claim 4, wherein the wavelength converter comprises a matrix material selected from the group consisting of $Gd_2O_3$, $Gd_2O2S$ and CsL.

6. The radiological imaging apparatus of claim 4, wherein the photoelectric converter comprises mainly amorphous silicon.

7. The radiological imaging apparatus of claim 4, wherein the radiation detection unit comprises:
   a switch for transmitting the electrical signal output from said photoelectric converter;
   a first wiring for connecting between said switch and said drive control unit; and
   a second wiring for connecting between said switch and said read-out unit,
   wherein said second wiring is connected to a first input of said first amplifier unit in said read-out unit.

8. The radiological imaging apparatus of claim 1, wherein the radiation detection unit is made of a material selected from the group consisting of amorphous silicon, gallium arsenic, mercury iodide and lead iodide.

9. A radiological imaging method for forming X-ray images using a radiological imaging apparatus having a radiation detection unit for converting radiation into one or more electrical signals, and a read-out unit for reading the electrical signals output by the radiation detection unit, wherein the read-out unit includes a first amplifier unit with variable gain, a control unit configured to control the gain of the first amplifier unit, a sample-hold unit disposed downstream of said first amplifier unit, configured to hold a signal amplified by said first amplifier, a multiplexer disposed downstream of said sample-hold unit, configured to convert parallel signals of output from the sample-hold unit into a serial signal, and a second amplifier unit disposed downstream of the multiplexer, wherein a frequency band of said first amplifier unit is narrower than that of said second amplifier unit, the method comprising the steps of:
   selecting between a still-picture mode and a moving-picture mode of the radiological imaging apparatus; and
   employing a variable gain control so that a gain Gf of the first amplifier unit during said moving-picture mode is set to be greater than a gain Gs of the first amplifier unit during said still-picture mode.

10. The radiological imaging method of claim 9, wherein, when imaging a still picture, a moving image is first acquired during the gain (Gf) is set to the first amplifier unit set in the moving-picture mode and then switches to the still-picture mode to set the gain (Gs) to the first amplifier unit so as to obtain a still image in response to a still picture imaging request.

* * * * *